US00PP19610P2

(12) United States Plant Patent
Verschoor

(10) Patent No.: US PP19,610 P2
(45) Date of Patent: Dec. 30, 2008

(54) PHLOX PLANT NAMED 'WATERMELON PUNCH'

(50) Latin Name: *Phlox paniculata hybrid*
Varietal Denomination: Watermelon Punch

(75) Inventor: Jan Verschoor, Haarlem (NL)

(73) Assignee: Witteman & Co, Hillegom (NL)

( * ) Notice: Subject to any disclaimer, the term of this patent is extended or adjusted under 35 U.S.C. 154(b) by 0 days.

(21) Appl. No.: 11/985,485

(22) Filed: Nov. 15, 2007

(51) Int. Cl.
*A01H 5/00* (2006.01)

(52) U.S. Cl. ..... Plt./320
(58) Field of Classification Search ..... Plt./320
See application file for complete search history.

*Primary Examiner*—Annette H Para
*Assistant Examiner*—S. B. McCormick Ewoldt
(74) *Attorney, Agent, or Firm*—Jondle & Associates, P.C.

(57) ABSTRACT

A new phlox plant particularly distinguished by salmon-pink petals around a large white center with a large floret diameter, a compact plant habit, healthy foliage and good mildew resistance is disclosed.

2 Drawing Sheets

Genus and species: *Phlox paniculata* hybid.
Variety denomination: 'Watermelon Punch'.

BACKGROUND OF THE NEW PLANT

The present invention comprises a new and distinct cultivar of phlox, botanically known as *Phlox paniculata,* and hereinafter referred to by the cultivar name 'Watermelon Punch'. The new cultivar originated from an open pollination in 2005 in Haarlem, The Netherlands between unknown male and female *Phlox paniculata* plants.

The new cultivar was selected from the results of the open pollination in 2006 in Haarlem, The Netherlands and has been asexually reproduced through two generations by vegetative cuttings in Haarlem, The Netherlands since that time. The present invention has been found to retain its distinctive characteristics through successive asexual propagations.

SUMMARY OF THE INVENTION

The following are the most outstanding and distinguishing characteristics of this new cultivar when grown under normal horticultural practices in Haarlem, The Netherlands.

1. Salmon-pink petals around a large white center;
2. Large floret diameter;
3. Compact habit;
4. Healthy foliage; and
5. Good mildew resistance.

DESCRIPTION OF PHOTOGRAPHS

This new phlox plant is illustrated by the accompanying photographs which show blooms and foliage of the plant in full color, the colors shown being as true as can be reasonably obtained by conventional photographic procedures. The photographs are of a 4-month-old plant grown in a greenhouse in Haarlem, The Netherlands.

DESCRIPTION OF THE NEW CULTIVAR

Figure 1:
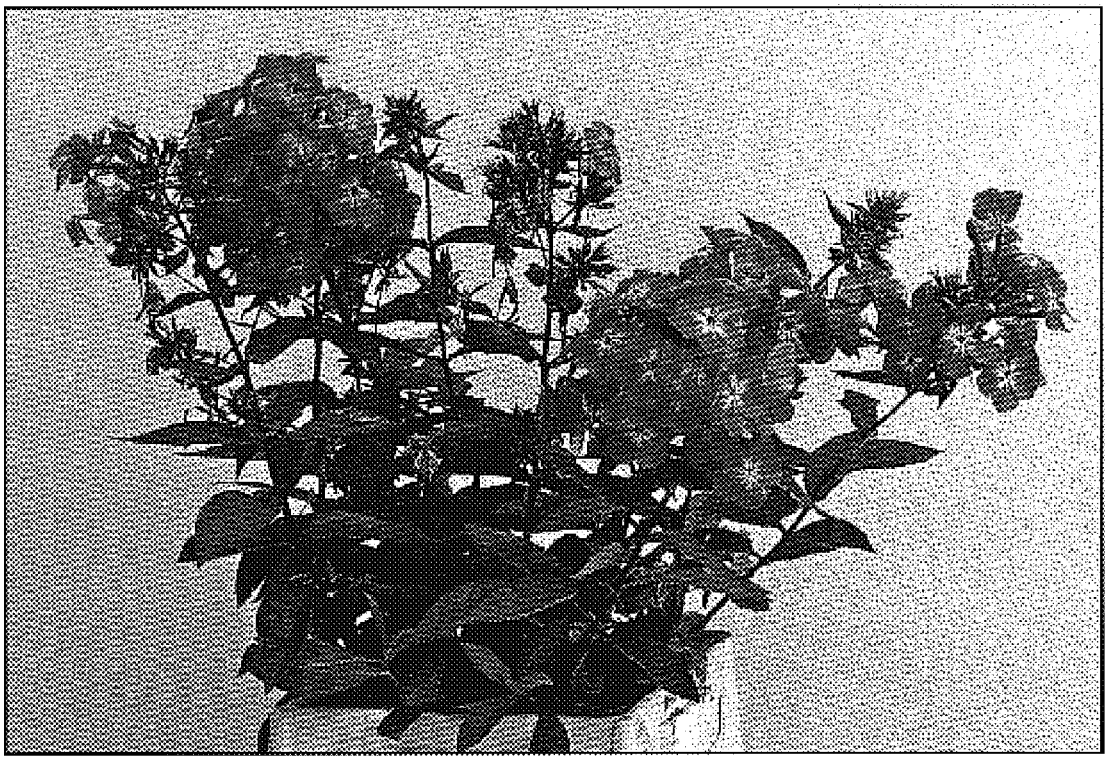
FIG. 1 shows the overall plant habit, including blooms, buds and foliage.
Figure 2:
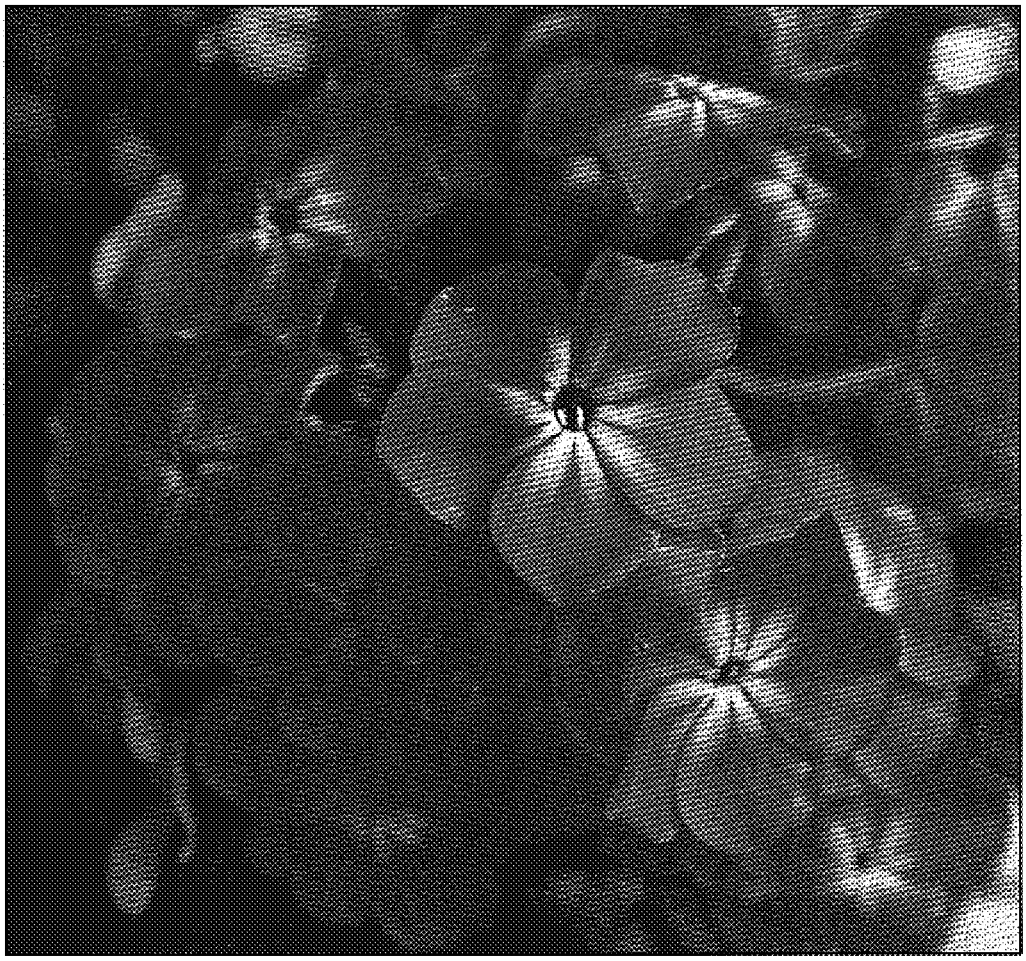
FIG. 2 shows a mature flower.
Figure 3:
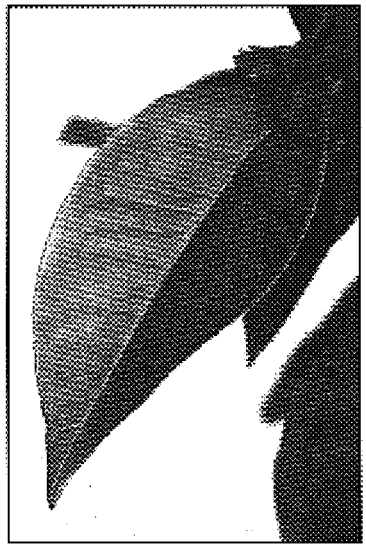
FIG. 3 shows a mature leaf of the plant.

The following detailed description sets forth the distinctive characteristics of 'Watermelon Punch'. The data which define these characteristics were collected from asexual reproductions carried out in Haarlem, The Netherlands. The plant history was taken in August on 2 year old plants which were planted and grown outdoors in daytime temperatures between 14° C. and 32° C., and nighttime temperatures between 5° C. and 15° C. No pinchings, growth retardants or photoperiodic treatments were used. Observations were made when the plants were in natural outdoor light. Color references are primarily to the R.H.S. Colour Chart of The Royal Horticultural Society of London (R.H.S.) (2001).

DETAILED BOTANICAL DESCRIPTION

Classification:
- *Family.*—Polemoniaceae.
- *Botanical.—Phlox paniculata.*
- *Common name.*—Phlox.

Parentage:
- *Female parent.*—Unknown.
- *Male parent.*—Unknown.

Growth:
- *Form.*—Herbaceous perennial.
- *Habit.*—Upright, moderately vigorous.
- *Shape.*—Inverted triangle.
- *Height (measured from the top of the soil).*—43.5 cm.
- *Diameter.*—49.5 cm.
- *Growth rate.*—10 cm per month.
- *Propagation.*—Terminal tips for cutting.
- *Time to produce a finished flowering plant.*—25 weeks from rooted cutting for a 1.5 liter container.
- *Time to initiate and develop roots during summer.*—30 days.
- *High temperature tolerance.*—Tolerant to at least 35° C.
- *Lower temperature tolerance.*—Hardy to USDA Zone 4.
- *Roots.*—White, thin, fibrous, sparse, freely branching.

Branches:

*Habit.*—Moderate basal branching.

*Number of branches.*—9 flowering stems.

Stems:

*Description.*—Round, glaborous, slightly glossy.

*Aspect.*—Rounded.

*Color.*—Between RHS N186C (Greyed-purple) to RHS 200A (Brown).

*Diameter.*—0.4 cm.

*Stem length* (*excluding inflorescence*).—30.7 cm.

*Internode length.*—3.2 cm.

*Pubescence.*—Absent.

Leaves:

*Arrangement.*—Opposite, single.

*Quantity of leaves* (*per lateral branch*).—20.

*Durability to stress.*—High.

*Shape.*—Broadly elliptical.

*Apex.*—Apiculate.

*Base.*—Obtuse.

*Color* (*mature leaves*).—Upper surface: Between RHS 137A (Green) to RHS 139A (Green). Lower surface: Between RHS 137B (Green) to RHS 137C (Green).

*Color* (*immature leaves*).—Upper surface: RHS 137A (Green). Lower surface: Between RHS 137C to RHS 138A (Green).

*Margin.*—Very short fine serrate (approx. 30 teeth per cm).

*Size.*—Length: 8.4 cm. Width: 3.8 cm.

*Texture* (*upper surface*).—Smooth, glabrous.

*Pubescence.*—Absent.

*Venation.*—Type: Pinnate. Color: Upper surface: Between RHS 144A (Yellow-green) to RHS 144B (Yellow-green). Lower surface: Between RHS 144B (Yellow-green).

*Petiole.*—Shape: V-shaped. Length: 0.4 cm. Diameter: 0.3 cm. Color: Upper surface: RHS 177A (Greyed-orange). Lower surface: Between RHS 144B (Yellow-green) to RHS 144C (Yellow-green).

Flower buds:

*Color.*—RHS 64B (Red-purple), lower half (immature calyx); between RHS 145A to RHS 145B (Yellow-green) at the base and between RHS 147A to RHS 147B at the tips; flushed with RHS N186C (greyed-purple).

Shape. —Narrow elliptic.

*Size.*—Length: 1.8 cm. Diameter: 0.45 cm

*Rate of opening.*—Open approximately 4 days from stage described above.

Inflorescence:

*Blooming habit.*—Continuous during natural flowering season.

*Inflorescence type.*—Self-cleaning, compound terminal panicle.

*Natural flowering season.*—Summer to late summer (July to late August).

*Height.*—14.7 cm.

*Width.*—12.1 cm.

*Aspect.*—Upright to outward.

*Fragrance.*—Present.

*Flower number* (*per inflorescence*).—150.

*Quantity of flowers per lateral stem.*—20.

*Quantity of flowers and buds per lateral stem.*—130.

*Quantity of flower buds per plant.*—1,500.

*Rate of flower opening.*—Approximately 30% of the flowers at any stage.

*Flower longevity on plant.*—10 days.

*Flower longevity as a cut flower.*—10 days.

Peduncle:

*Color.*—Between RHS N186C (Greyed-purple) to 200A (Brown).

*Length.*—Primary: 15.1 cm. Secondary: 4.5 cm.

*Diameter.*—Primary: 0.25 cm. Secondary: 0.15 cm.

*Angle.*—Primary peduncles average angle 0° (straight upright), secondary peduncles with an average angle of 55°.

*Strength.*—Strong.

Pedicel:

*Color.*—Between RHS 146A to RHS 147A (Yellow-green).

*Length.*—0.7 cm.

*Diameter.*—0.1 cm.

*Angle.*—Average angle 30° (0° to 60°) (0°=straight on top of the peduncle).

*Strength.*—Strong.

Florets:

*Type.*—Single.

*Shape.*—Salverform.

*Fragrance.*—Moderate, sweet; typical *Phlox paniculata* scent.

*Size.*—Height (flower depth): 2.7 cm. Diameter: 3.8 cm.

*Corolla.*—Tube shape. Color: Inside: RHS 64A. Outside: RHS 70C. Length: 1.3 cm. Diameter: 0.15 cm.

*Petals.*—Arrangement: Rotate. Shape: Spathulate, the lower 60% fused into a tube. Appearance: Dull, smooth. Number: 5, fused at the base (lower 60% of each petal). Size: Length: 4.2 cm (lower 2.5 cm fused into a tube). Width: 1.7 cm. Apex: Rounded. Base: Fused. Margin: Entire. Color (when opening): Upper surface: RHS 52A (Red); base of free part between RHS N74A to RHS N74D (Red-purple); tube RHS N79C (Purple). Lower surface: Between RHS 55B to RHS 55C (Red); tube RHS N79C (Purple). Color (fully opened): Upper surface: RHS 52B (Red); base of free part between RHS 69C to RHS 69D (Red-purple); tube RHS N79C (Purple). Lower surface: Between RHS 55B to RHS 55C (Red); tube RHS N79C (Purple). Color fading to: RHS 55A (Red); base of free part between RHS 69C to RHS 69D (Red-purple); tube RHS N79C (Purple). Petal texture (both surfaces): Smooth.

Calyx:

*Shape.*—Campanulate.

*Length.*—0.9 cm.

*Diameter.*—0.5 cm.

*Sepals.*—Arrangement: Rotate. Appearance: Smooth, dull. Number: 5. Shape: Linear. Apex: Narrow apiculate. Base: Lower 60% fused. Margin: Entire. Size: Length: 0.9 cm. Width: 0.2 cm. Color (mature): Upper surface: Between RHS 145A to RHS 145B (Yellow-green) at the base; between RHS 147A to RHS 147B at the tips; flushed with RHS N186C (Greyed-purple). Lower surface: RHS 145B (Yellow-green) at the base; RHS 147B at the tips. Color (immature): Upper surface: Between RHS 145A to RHS 145B (Yellow-green) at the base; between RHS 147A to RHS 147B at the tips; flushed with RHS N186C (Greyed-purple). Lower surface: RHS 145B (Yellow-green) at the base; RHS 147B at the tips.

Reproductive organs:

*Stamens.*—Quantity: 5. Anther: Shape: Basifixed, oblong; filament implanted in petal. Length: 0.2 cm. Length of filament: 0.1 cm. Color: RHS 4D (Yellow).

*Pollen.*—Amount: Moderate. Color: RHS 4C (Yellow).

*Pistil.*—Quantity: 1. Length: 2.1 cm.

*Style.*—Length: 1.9 cm. Color: Between RHS 187B to 187C (Greyed-purple).

*Stigma.*—Shape: Cleft (3-parted). Color: RHS 150D (Yellow-green).

*Ovary color.*—RHS 143A.

Fruit and seed set:

*Seed.*—Quantity: 3 seeds per fruit. Length: 0.3 cm. Diameter: 0.2 cm. Color: RHS 200A (Brown).

*Fruit.*—Quantity per lateral branch: 5. Quantity of fruit per plant: 45. Length: 1.2 cm. Diameter: 0.6 cm. Color: RHS 146A (Yellow-green). Texture: Smooth, glossy.

Disease and insect resistance: No particular resistance or susceptibility to diseases or insects noted to date.

COMPARISON WITH COMMERCIAL CULTIVARS

'Watermelon Punch' differs from the commercial *Phlox paniculata* variety 'Rainbow' (unpatented), by having a sturdier plant with healthier foliage and thicker stems than 'Rainbow'. 'Watermelon Punch' is a more compact plant than 'Rainbow'. Additionally, 'Watermelon Punch' has more even and richer flowers with salmon-pink petals around a large white center while 'Rainbow' has uneven and less rich flowers with purple-pink petals with a white center.

'Watermelon Punch' differs from the commercial *Phlox* variety 'Grenadine Dream' (unpatented), by having salmon-pink petals while 'Grenadine Dream' has rich red-purple petals.

I claim:

1. A new and distinct cultivar of phlox plant as shown and described herein.

* * * * *